(12) United States Patent
Berky et al.

(10) Patent No.: US 6,193,652 B1
(45) Date of Patent: **\*Feb. 27, 2001**

(54) TISSUE STABILIZATION DEVICE FOR USE DURING SURGERY HAVING SPHERICAL CURVED FEET

(75) Inventors: Craig B. Berky, Milford; William D. Fox, New Richmond; Gary W. Knight, West Chester; David L. Hamann, Cincinnati, all of OH (US)

(73) Assignee: Ethicon Endo-Surgery, Inc., Cincinnati, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/946,455

(22) Filed: Oct. 7, 1997

(51) Int. Cl.$^7$ .................................................. A61B 1/26
(52) U.S. Cl. .................... 600/205; 600/201; 600/229; 600/231; 600/235
(58) Field of Search .................... 600/228, 249, 600/235, 229, 231, 205, 201; 604/180, 27; 128/200.26; 606/15

(56) References Cited

U.S. PATENT DOCUMENTS

| | | | |
|---|---|---|---|
| Re. 34,150 | 12/1992 | Santilli et al. ............. | 128/20 |
| 2,082,782 | 8/1937 | Allen ....................... | 128/20 |

(List continued on next page.)

FOREIGN PATENT DOCUMENTS

| | | | | |
|---|---|---|---|---|
| 29713569 | * | 2/1998 | (DE) . | |
| 0 791 329 A1 | * | 8/1997 | (EP) . | |
| 0 791 330 A2 | * | 8/1997 | (EP) . | |
| 2 214 428 | | 6/1989 | (GB) ............. | A61B/19/00 |
| 1378822 | * | 3/1998 | (SU) ............. | 600/231 |
| WO 97/10753 | * | 3/1997 | (WO) . | |
| WO 98/17182 | | 4/1998 | (WO) ............. | A61B/17/02 |

OTHER PUBLICATIONS

"Experimental videothorascoscopic cannulation of the left atrial appendix", P. F. Grundeman, D.W. Meijer, J.J.G. Bannenberg, R. Tukkie and P.J. Klopper, pp. 511–513.

*Primary Examiner*—Sharon Kennedy
*Assistant Examiner*—Kevin C Sirmons

(57) ABSTRACT

In accordance with the present invention there is provided a device for stabilizing and/or manipulating moving tissue, such as a beating heart, so as to facilitate surgical procedures on such tissues. The device includes a tube having a proximal end, a distal end and a lumen extending therebetween. The tube is operatively connected to a suction source so as to draw air through the tube from the distal end to the proximal end. The device further includes at least one foot operatively connected to the distal end of the tube. The foot extends laterally from the tube. In a preferred embodiment the device includes a pair of feet which are spaced apart laterally from each other. Each foot has a proximal surface, and a distal surface for making contact with the tissue. The distal surface of each foot has an outer perimeter having a substantially spherical profile. This spherical profile helps the device make better contact with the tissue, so the tissue can be more effectively manipulated.

34 Claims, 13 Drawing Sheets

U.S. PATENT DOCUMENTS

| | | | |
|---|---|---|---|
| 3,626,471 | 12/1971 | Florte | 128/20 |
| 4,047,532 | 9/1977 | Phillips et al. | 128/303 |
| 4,049,000 | 9/1977 | Williams | 128/276 |
| 4,143,652 | 3/1979 | Meier et al. | 128/20 |
| 4,457,300 | 7/1984 | Budde | 128/20 |
| 4,617,916 | 10/1986 | de Vahn et al. | 128/20 |
| 4,627,421 | 12/1986 | Symbas et al. | 128/20 |
| 4,637,377 | 1/1987 | Loop | 128/1 R |
| 4,726,356 | 2/1988 | Santilli et al. | 128/20 |
| 5,108,412 | 4/1992 | Krumeich | 606/166 |
| 5,171,254 | 12/1992 | Sher | 606/166 |
| 5,392,764 | 2/1995 | Swanson et al. | 128/3 |
| 5,509,890 * | 4/1996 | Kazama . | |
| 5,545,123 * | 8/1996 | Ortiz et al. | 600/235 |
| 5,547,473 * | 8/1996 | Peyman | 604/27 |
| 5,562,658 * | 10/1996 | Long | 606/15 |
| 5,582,580 * | 12/1996 | Buckman, Jr. et al. . | |
| 5,588,952 * | 12/1996 | Dandolu | 600/249 |
| 5,595,172 * | 1/1997 | Reese | 128/200.26 |
| 5,643,217 * | 7/1997 | Dobkin | 604/180 |
| 5,727,569 * | 3/1998 | Benetti et al. | 604/180 |
| 5,749,892 | 5/1998 | Vierra | 600/204 |
| 5,782,746 | 7/1998 | Wright | 600/37 |
| 5,865,730 * | 2/1999 | Fox et al. | 600/228 |
| 6,007,486 * | 12/1999 | Hunt et al. | 600/205 |

* cited by examiner

TISSUE STABILIZATION DEVICE FOR USE DURING SURGERY HAVING SPHERICAL CURVED FEET

FIELD OF THE INVENTION

The present invention relates to the field of surgery. More specifically, the present invention generally relates to surgical devices that stabilize or temporary immobilize moving tissue during a surgical procedure. The present invention has even further relation to such devices that are used to stabilize a beating heart during cardiovascular surgery.

BACKGROUND OF THE INVENTION

There are many types of surgical procedures where the surgeon must perform various operations on moving organs or tissue within the human body. For example, there has recently been an effort to perform coronary artery bypass surgery on a beating heart, without using cardiopulmonary bypass and a heart-lung machine. During a typical coronary bypass procedure, a bypass graft is used to help reestablish coronary artery circulation when a portion of the coronary artery is stenosed. Typically the graft vessel used in bypassing the stenosed portion of the coronary artery comprises one or more segments of the patient's saphenous vein or internal mammary artery.

Once the graft vessel is harvested and prepared, one end is sutured to the aorta, near its base, and the other end is attached to the coronary artery, just distal to the blockage. Some surgeons choose to complete all the proximal anastomosis, to the aorta, before commencing the distal anastomosis to the coronary arteries. In contrast, others choose to complete the distal anastomosis first. Regardless of the order, when undertaking the distal anastomosis to the coronary artery, it is important that the vessel graft be held steady and adjacent the coronary artery, with a minimum of vascular trauma and a minimum of visual and surgical obstruction by instruments in the narrow operative field.

The speed of performing such anastomosis can become extremely critical as well, especially during procedures where the heart is kept beating. Often the coronary artery is occluded during the procedure to reduce blood loss through the arteriotomy. It is very important to reconnect the supply of blood to the artery as soon as possible in order to minimize or prevent damage to the patient such as damage to the myocardium. Blood vessels are now normally anastomosed end-to-end or end-to-side by suturing techniques. Conventionally, to suture two vessels together, a surgeon passes the pointed tip of a curved suturing needle, having a suture attached to the blunt end, through the coronary artery, into the lumen of the vessel and back out through the graft vessel. Then, the surgeon grasps the tip of the needle which has been forced through the tissues with fingers or a needle holder and pulls the needle through the tissues, wherein the suture follows the curved path of the needle. Usually a knot or button is present at the trailing end of the suture to anchor the first stitch. After the surgeon has pulled the suture entirely through the tissues to tension the first stitch, he or she then forces the tip of the needle through the coronary artery again, at a location spaced from the first stitch, until the needle again goes through the coronary artery, into the lumen of the vessel and back out through the graft vessel. Again, he grasps the tip of the needle which has been forced through the tissues, applies tension to the needle pulls the entire suture through the tissues to complete the second stitch. This process is repeated again and again, with the surgeon tensioning the suture after each stitch to draw the tissues together thereby creating a running or continuous stitch, composed of individual thread loops, which extends around the graft vessel.

Needless to say, performing vessel anastomosis, such as described above, can become very difficult, especially when performed on a beating heart. Suture anastomosis procedures on non-beating hearts generally take the skilled surgeon anywhere from ten to twenty minutes to complete for each anastomosis. Therefore, there has been some attempts to provide a device for stabilizing or immobilizing a portion of the heart, preferably a portion near the anastomosis site, so that the surgeon can more readily complete the bypass procedure. In the past the surgeon would use a pair or forceps or a metal fork-type device to push against a portion of the heart, near the anastomosis site to keep the heart relatively still so that bypass procedure could be performed.

Another type of stabilization device is called a "vacuum based" device. The benefit of vacuum based devices is that they have members which grab onto a portion of the heart by suction and lift it up in order to immobilize it. This is often a better method of stabilizing the beating heart. An example of such a device is given in PCT International Publication Number WO 97/10753, published on Mar. 27, 1997 and which is hereby incorporated herein by reference. However, this device has many disadvantages, including a low integrity vacuum seal between the device and the heart caused by any number of reasons including particulate being trapped in the vacuum tube.

SUMMARY OF THE INVENTION

In accordance with the present invention there is provided a device for stabilizing and/or manipulating moving tissue, such as a beating heart, so as to facilitate surgical procedures on such tissues. The device includes a tube having a proximal end, a distal end and a lumen extending therebetween. The tube is operatively connected to a suction source so as to draw air through the tube from the distal end to the proximal end. The device further includes at least one foot operatively connected to the distal end of the tube. The foot extends laterally from the tube. In a preferred embodiment the device includes a pair of feet which are spaced apart laterally from each other. Each foot has a proximal surface, and a distal surface for making contact with the tissue. The distal surface of each foot has an outer perimeter having a substantially spherical profile. This spherical profile helps the device make better contact with the tissue, so the tissue can be more effectively manipulated.

It should be understood that the present invention is not limited to vacuum based devices. Many of the advantages offered by this invention are equally applicable to when the device is used as a mechanical device. That is when the is pressed against the heart for stabilization. In this embodiment, the tube could be replaced by a longitudinal member which could be solid.

BRIEF DESCRIPTION OF THE DRAWINGS

The foregoing and other aspects of the present invention will best be appreciated with reference to the detailed description of the invention in conjunction with the accompanying drawings, wherein.

The drawings are not necessarily to scale.

DETAILED DESCRIPTION OF THE INVENTION

In surgery on the heart or other organs of the body, the surgeon must first make an incision through several layers of tissue to achieve access to the organ, and the opening created must be held open during the duration of the surgery. Surgical retractors are well-known in the surgical art, several examples being illustrated in U.S. Pat. No. 4,617,916 issued to Le Vahn et al. on Oct. 21, 1986; and U.S. Pat. No. 4,627,421 issued to Symbas et al on Dec. 9, 1986, both of which are hereby incorporated herein by reference. One common element of these retractors is a metal cross-bar which may vary in cross-sectional dimensions, but is generally, but not exclusively, rectangular, and is about 0.12–0.25 inches thick by 0.5–1.9 inches wide. In the case of minimally invasive, direct coronary artery bypass (MIDCAB) surgery, a mini-thoracotomy is created with an incision through the chest wall about 10 cm long running in the intercostal space between the ribs over the heart. The retractor is then inserted into the narrow opening created, and the ribs and tissues are spread apart through adjustment of the retractor, thus exposing the heart.

Figure 1:
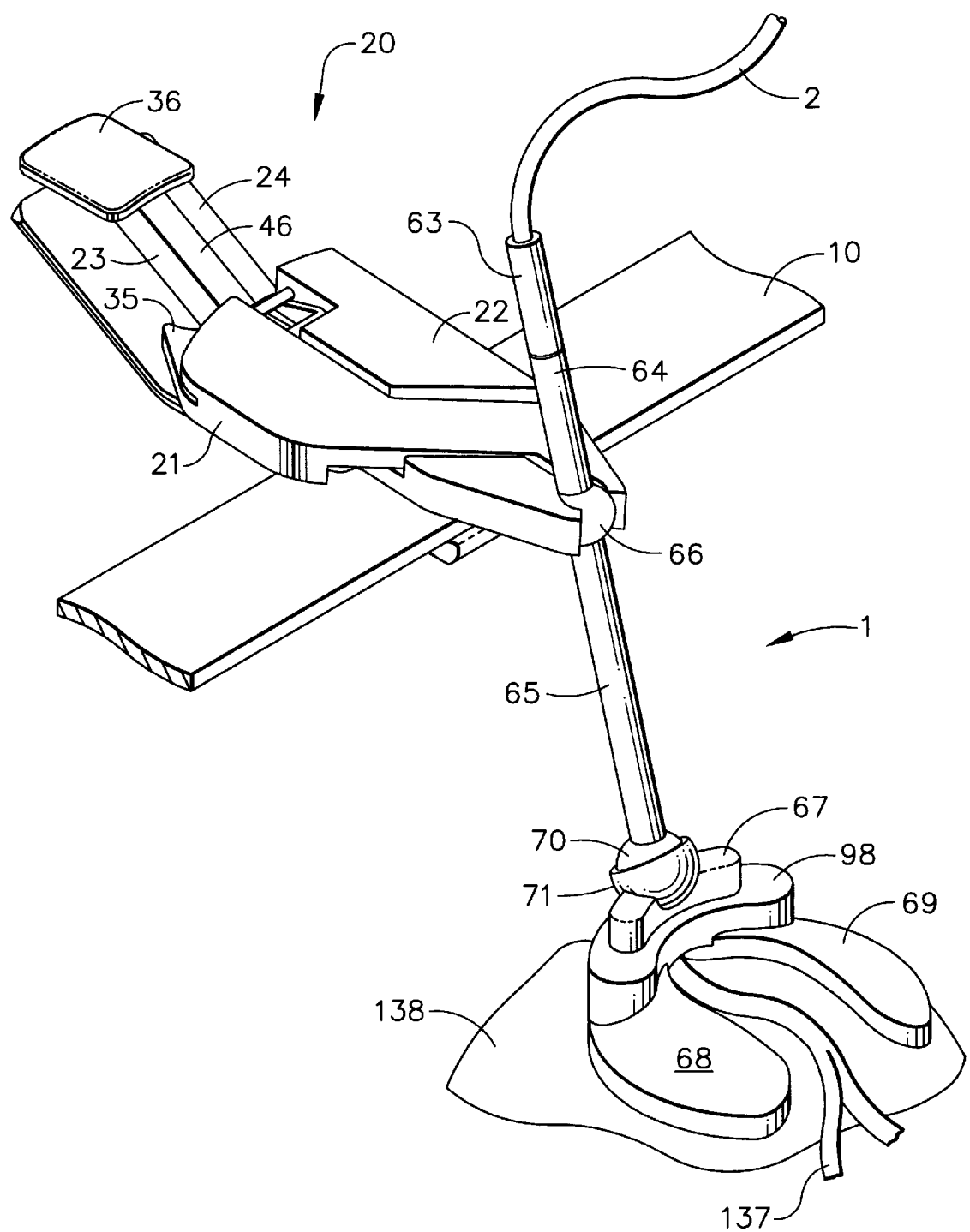
FIG. 1 is a view of the present invention being used in combination with an adjustable retractor (partially shown) in surgery to temporarily immobilize a local area of heart tissue in which access to the heart is achieved through a mini-thoracotomy.
Figure 2:
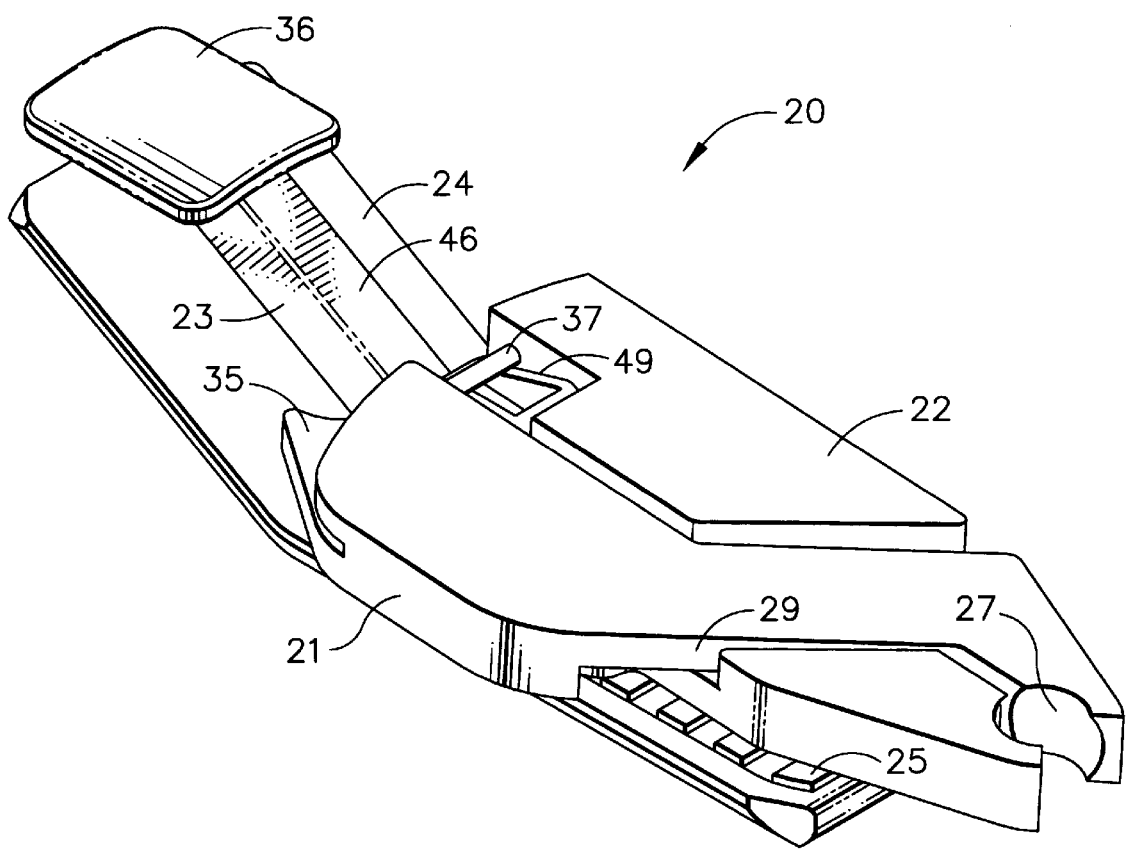
FIG. 2 is a perspective view of the retractor mount shown in FIG. 1.
Figure 3:
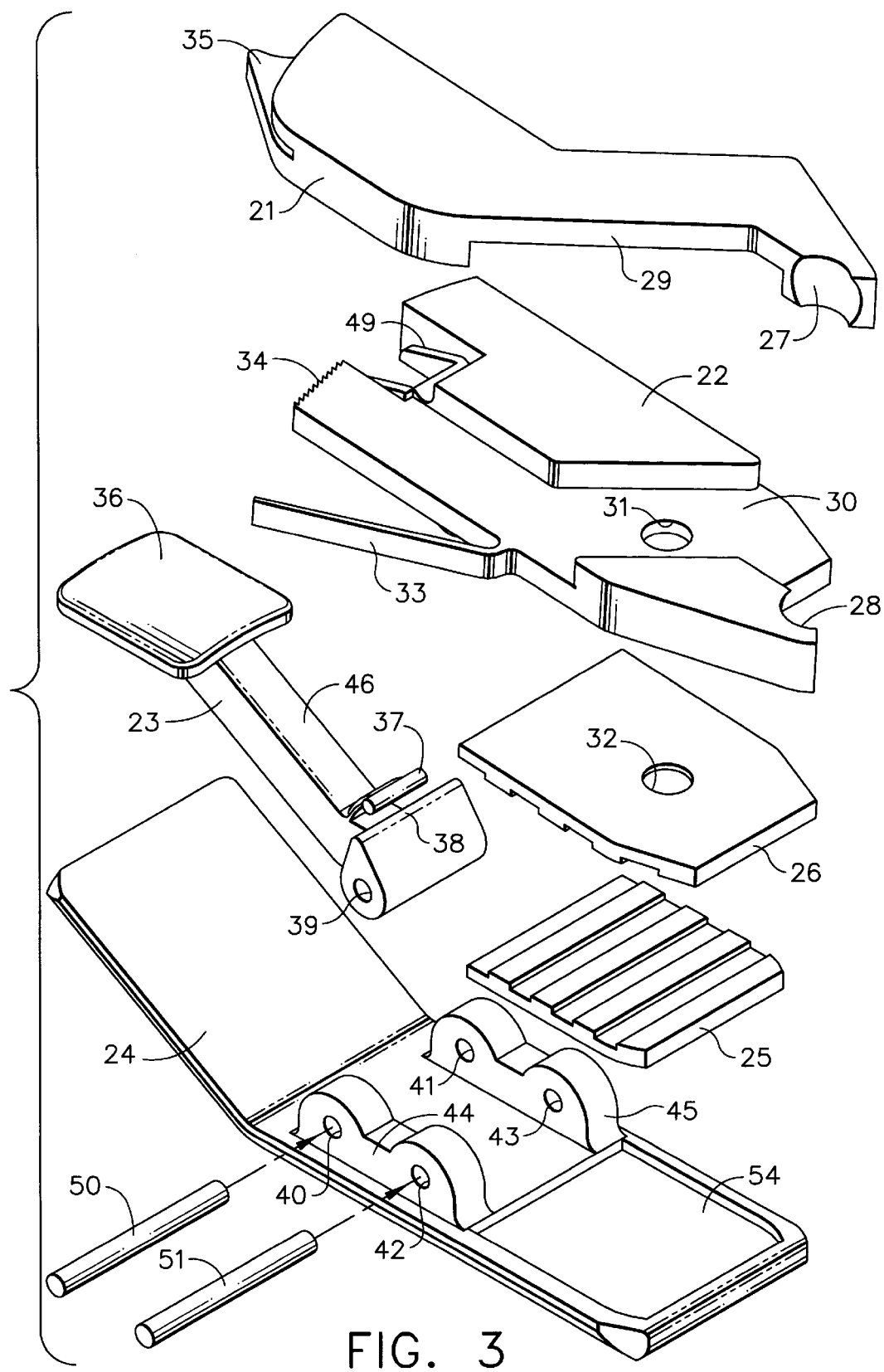
FIG. 3 is an exploded, perspective view of the components of the retractor mount depicted in FIG. 2.

Referring to FIG. 1 which depicts the preferred embodiment of the present invention, the device is comprised of the stabilizer 1 and the retractor mount 20 and are shown attached to the surgical retractor bridge bar 10 (partial view). The stabilizer is attached to a suction source by a flexible hose 2. The distal portion of the stabilizer is shown in contact with the organ 138 being stabilized and consisting of a left foot 69 and a right foot 68 which in some cases may be placed to straddle a vessel 137 to be operated on. The left and right feet 69, 68 are somewhat like clamshells in that they are generally hollow and crescent shaped. When the organ is in complete contact with the edge along the entire perimeter of each foot, and when a suction source is communicated to each foot via air passages through the stabilizer 1, the feet 69, 68 maintain enhanced attachment to the organ. The gripping force required depends on the seal created and the vacuum level. A significant amount of stabilization of the organ could also be achieved without the suction source by simply holding the stabilizer firmly against the heart surface and attaching it to the retractor mount 20. Again in FIG. 1, it can be seen that the stabilizer 1 is attached to the retractor mount 20 which, in turn, is removably attached to the retractor bridge bar 10. Also shown is distal ball 70 which allows angular and rotational movement of the distal portion of the stabilizer with respect to the lower stem 65, and a proximal ball 66 which allows rotational, angular, and longitudinal movement of the stabilizer 1 with respect to the retractor mount. As a result, it is possible to accommodate large variations in the position of the organ relative to the surgical retractor bridge bar 10 location and orientation. This is important due to the wide range of surgical patient sizes, differences in anatomy, and variations in surgical technique.

Turning to FIGS. 2, 3, 4, 5 and 6, the retractor mount 20 consists of six main components: the mount base 24, the mount top 22, the cam lever 23, the ball clamp arm 21, the upper gripping pad 26, and the lower gripping pad 25. Many of these components may be made of metal such as a stainless steel in order to be reusable and sterilizable in a steam autoclave, but in the preferred embodiment, components 21, 22, 23, 24 are made of plastic such as a medical grade rigid plastic polycarbonate. The gripping pads 25, 26 may also be made of plastic also, but the preferred material is an elastomer such as polyurethane. The cam lever 23 is hinged to base 24 by first pin 50 through holes 40, 41 and 39. Mount top 22 is hinged to the base 24 by second pin 51 through holes 42, 43 and 52. Ball clamp arm 21 is pivotably attached to mount top 22 by an integral, spring post 53 on the mating surface of ball clamp arm 21 into hole 31 of the mount top 22. Gripping pad 25 is retained in base 24 by an undercut recess 54 in base 24. Gripping pad 26 is retained in mount top 28 by a similar means.

Figure 4:
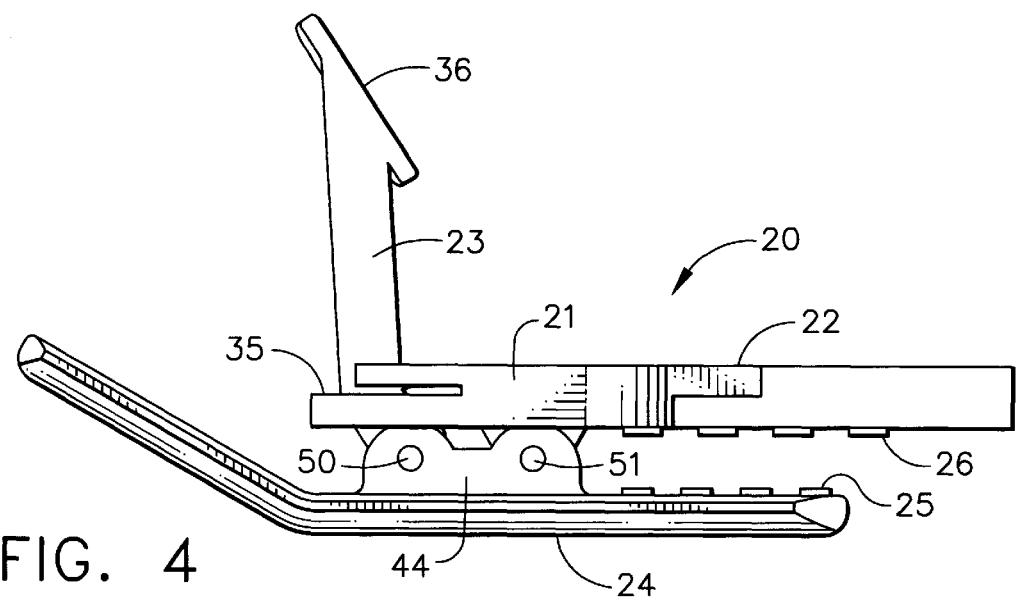
FIG. 4 is a side view of the retractor mount shown in FIG. 2.
Figure 5:
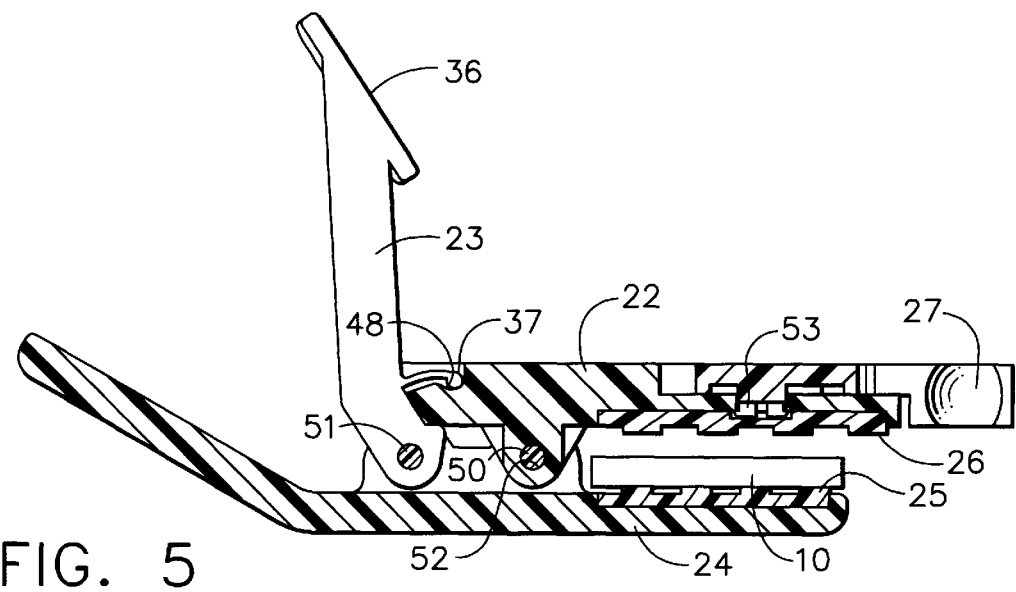
FIGS. 5 and 6 are cross-sectional views of the retractor mount depicted in FIG. 2 and show the latched and unlatched positions of the stabilizer mount as it is being attached to the retractor.
Figure 6:
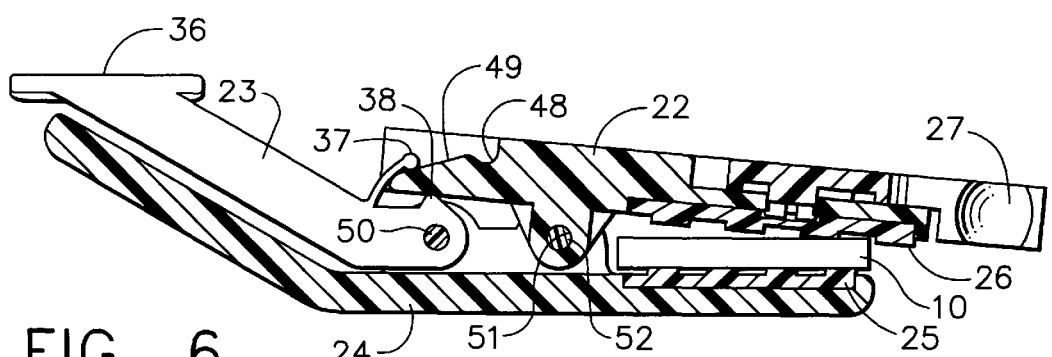

It is often necessary during the surgical procedure to reposition the stabilizer, and this may easily be accomplished in this invention by using the two adjustment features of the stabilizer mount 20. Referring again to FIGS. 4, 5, and 6, the adjustment method is described for attachment of the retractor mount 20 to the retractor bridge bar 10. FIG. 4 shows the front view of the retractor mount 20 while the cam lever 23 is in the open position and before the retractor mount 20 is placed onto the bridge bar 10. In FIG. 5, a longitudinal cross-section through the components except for the cam lever 23 depicts positioning of the retractor mount 20 on the bridge bar 10. This view also reveals how finger 37 locates into detent recess 48 in order to hold the cam lever 23 in the open position. In this position, the mount top 22 is essentially parallel to the base 24, thus creating clearance between the gripping pads 25, 26 and the retractor bridge bar 10. In FIG. 6, the cam lever 23 is shown in the closed position which is accomplished by the user squeezing lever pad 36 and base 24 together. When the cam lever beam 46 abuts base 24, cam surface 38 will have pivoted to a locking position against the underside of the mount top 22, thus causing mount top 22 to have pivoted about second pin 51 to the extent that gripping pads 25, 26 are compressed against bridge bar 10. This separating force acting between the base 24 and the mount top 22 at the bridge bar 10 causes the cam lever 23 to remain in the locked position so that the retractor mount cannot move about on the bridge bar 10. To unlock the retractor mount 20 from the bridge bar 10, an upward force may be applied by the user to the cam lever pad 36 until cam surface 38 has pivoted sufficiently to reverse the rotational moment on the cam lever 23, causing it to then pop open. During the clamping process described, the spherical clamping surface 27 of the cam lever 23 and the spherical clamping surface 28 of mount top 22 are extended beyond the edge of base 24 so that clearance is allowed for assembly of stabilizer 1 to the retractor mount 20. These spherical clamping surfaces 27, 28 are aligned in order to hold firmly onto proximal ball 66 of the stabilizer 1, shown in FIG. 1.

Figure 7:
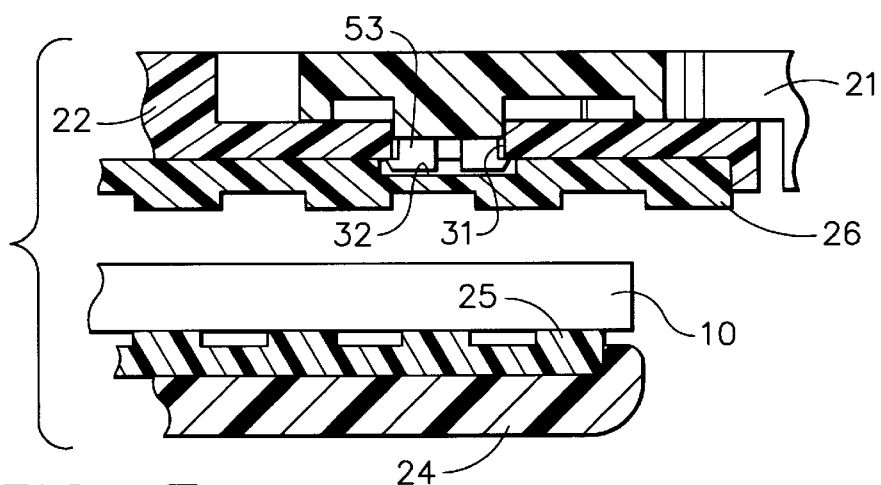
FIG. 7 is an enlarged, cross-sectional view of a portion the retractor mount depicted in FIG. 5.

FIG. 7 shows an enlarged, cross-sectional view of the portion of the retractor mount 20 as it was depicted in FIG. 5. This view shows more clearly than in FIG. 5 the spring post 53 as it is snapped into hole 31 and partially projecting into recess 32 of gripping pad 26.

Figure 8:
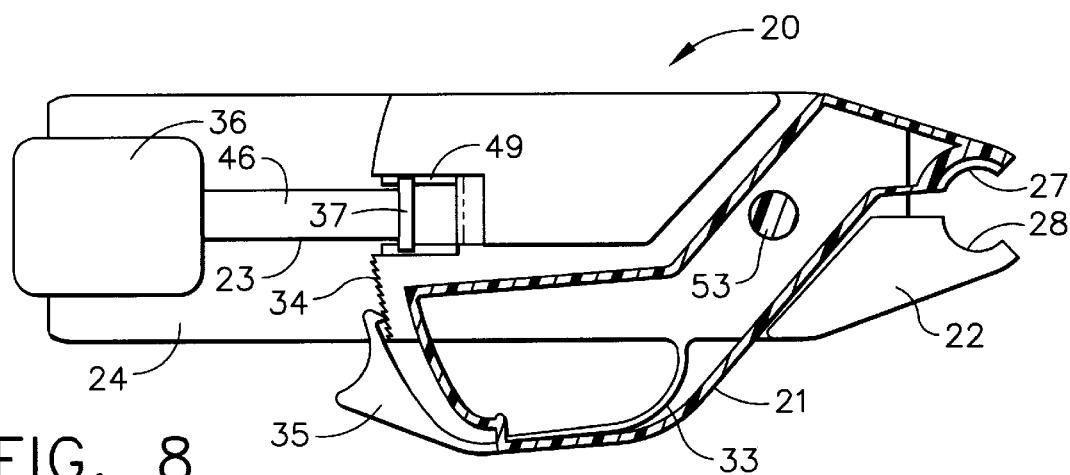
FIGS. 8 and 9 show top views of the stabilizer mount depicted in FIG. 2 and show two positions of the tightness adjustment of the retractor mount attachment to the stabilizer depicted in FIG. 1.
Figure 9:
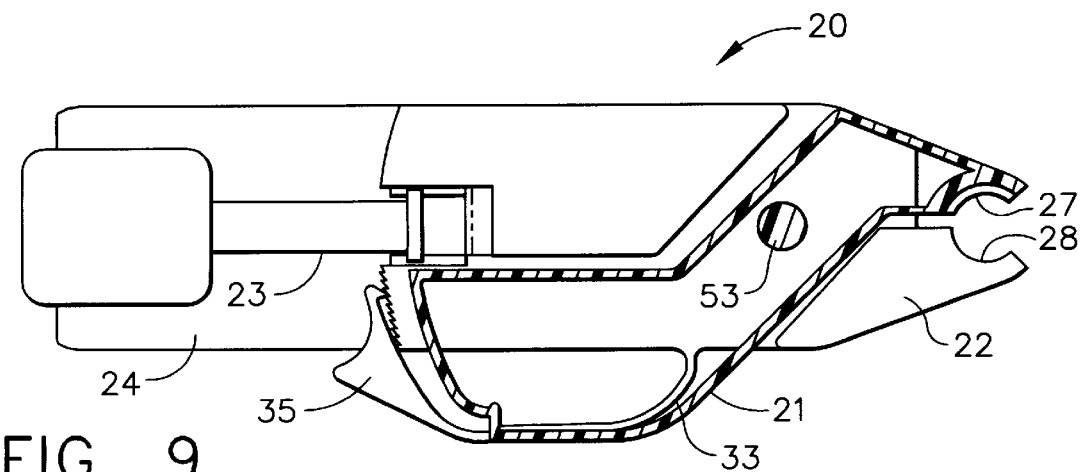

Turning now to FIGS. 8 and 9, the top view of retractor mount 20 is shown for two positions of the ball clamp arm 21, which has ratchet pawl 35 shown in engagement with ratchet teeth 34 on mount top 22. The spherical clamping surfaces 27 and 28 are seen in the open or loose position to allow movement of proximal ball 66 (FIG. 1) within. When the user squeezes ball clamp arm 21 together with mount top 22, the ball clamp arm 21 pivots about spring post 53, and the distance between spherical surfaces 27, 28 is reduced, thus holding proximal ball 66 firmly. The leaf spring 33 on the mount top 22 exerts an opening force against the ball clamp arm 21 so that when ratchet pawl 35 is pulled away from ratchet teeth 34 by the user, the ball clamp arm 21 releases the ball 66, allowing movement of the stabilizer 1 while still captured in the retractor mount 20.

Figure 10:
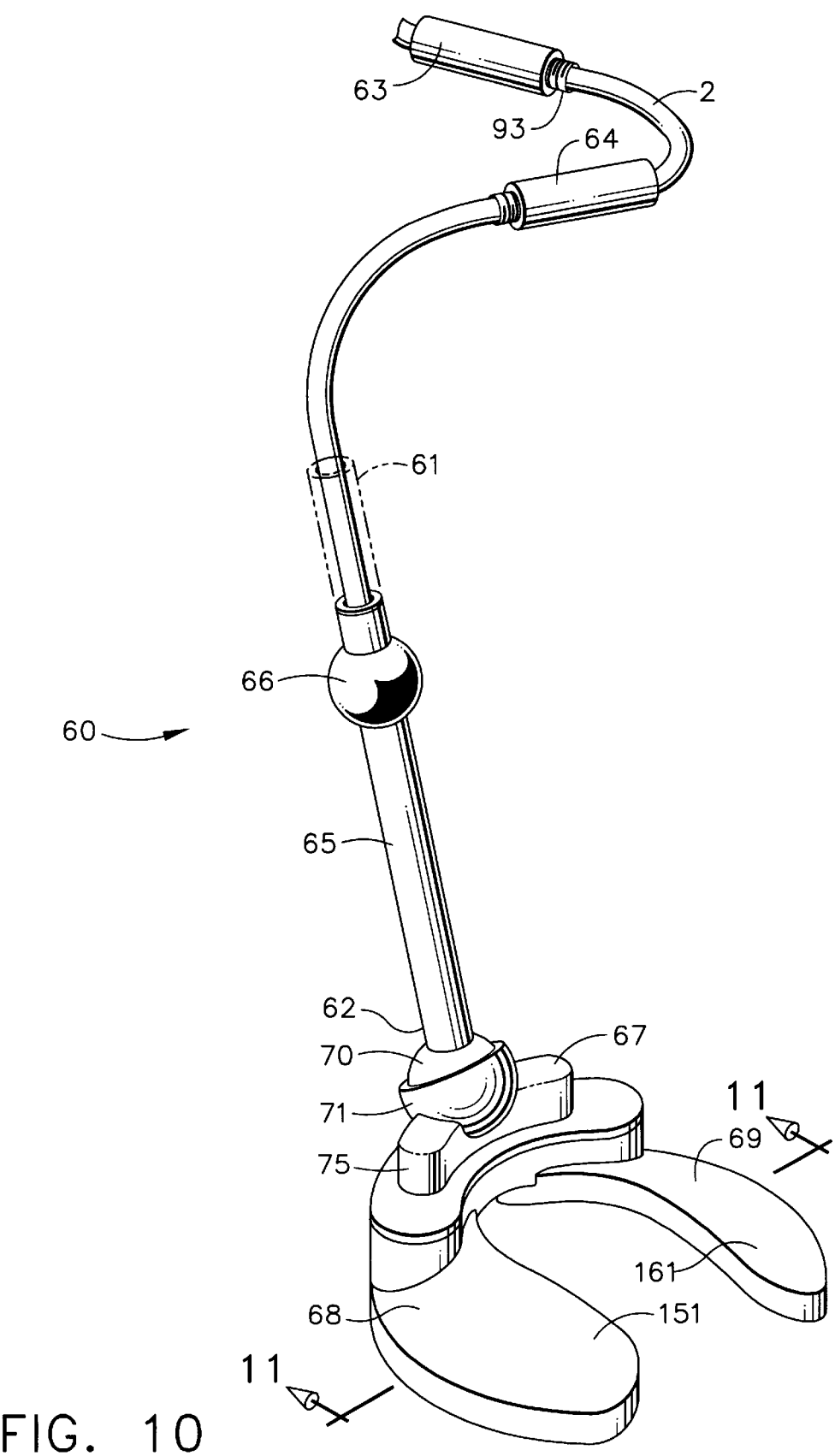
FIG. 10 is a perspective view of the stabilizer depicted in FIG. 1.

FIG. 10 shows the preferred embodiment of the stabilizer 1 which was depicted in FIG. 1. Stabilizer 1 includes a tube, or longitudinal member, 60 having a proximal end 61, a distal end 62 and a lumen extending therebetween (not shown). Tube 60 is connected to a suction source by tube 2 so as to draw air from the distal end 62 to the proximal end 61. Tube 60 can include a number of stems which are detachable from each other. FIG. 10 shows tube 60 as having a first upper stem 63, a second upper stem 64 and a lower stem 65. Stem 63 has been detached from the second upper stem 64 and moved proximally on flexible hose 2. Stem 63 and 64 can be connected to each other by a threaded engagement, a frictional push fit engagement or any other means well known to those of ordinary skill in the art. FIG. 10 shows an external screw thread 93 on the distal end of the first upper stem 63 which would be attached to an internal thread on the proximal end of the second upper stem 64. The user would detach the two by rotating the first upper stem 63 while holding the second upper stem 64.

This feature allows portions of the tube 60 to be removed from the surgeons working area causing less obstruction during the procedure. The lumens through the upper stems 63, 64 are large enough to slide freely over the flexible hose 2, which is attached to the lower stem 65, and put out of the way. Second upper stem 64 can be detached from lower stem 65 in a similar manner, and moved proximally. The number of such stems may vary, depending on the desired length of the original assembly, the means of attachment to one another, and the ease of handling the individual components during a surgical procedure. Detaching these would typically be done after the adjustments on the retractor mount 20 have been made and the stabilizer feet 68, 69 are located properly on the organ. As mentioned above, this ability to detach the upper stems 63, 64 is advantageous in allowing improved access and visibility to the surgical site for the surgeon. By keeping the upper stems 63, 64 captured on the flexible hose 2, it is easy for the users (scrub nurse, etc.,) to keep track of the components or to reassemble them to the stabilizer 1 during the procedure if it is determined that the overall length of the stabilizer 1 is too short.

As described earlier, the proximal ball 66 may slide freely over stems 63, 64, 65 until the ball clamp arm 21 is locked in the closed position. This is because the proximal ball 66 is made of a material, preferably plastic, which is flexible enough to be compressed onto the stems 63, 64, 65, yet the hole through it is just large enough to allow it to move freely on the stems 63, 64, 65 when not compressed. All the components of the stabilizer 1 shown in FIG. 10 may be made of metal such as stainless steel, or plastic, except the flexible tube which is made of a medical grade, tubing material such as silicone or polyurethane. The preferred material for the feet 68, 69 and the bridge 75, all of which may be injected molded as one piece, is a plastic such as polycarbonate or polyethylene. This is true also for the manifold 67 and the stems 65, 64, 63. The distal end of the lower stem 65 has an integrally molded, distal ball 70 which fits tightly into a spherical cup or socket 71 feature of the manifold 67. This joint is tight enough to maintain its seal of the air passage through it and the orientation of the stabilizer 1 during the surgical procedure, yet loose enough to be adjusted easily by manipulation by the user.

Figure 11:
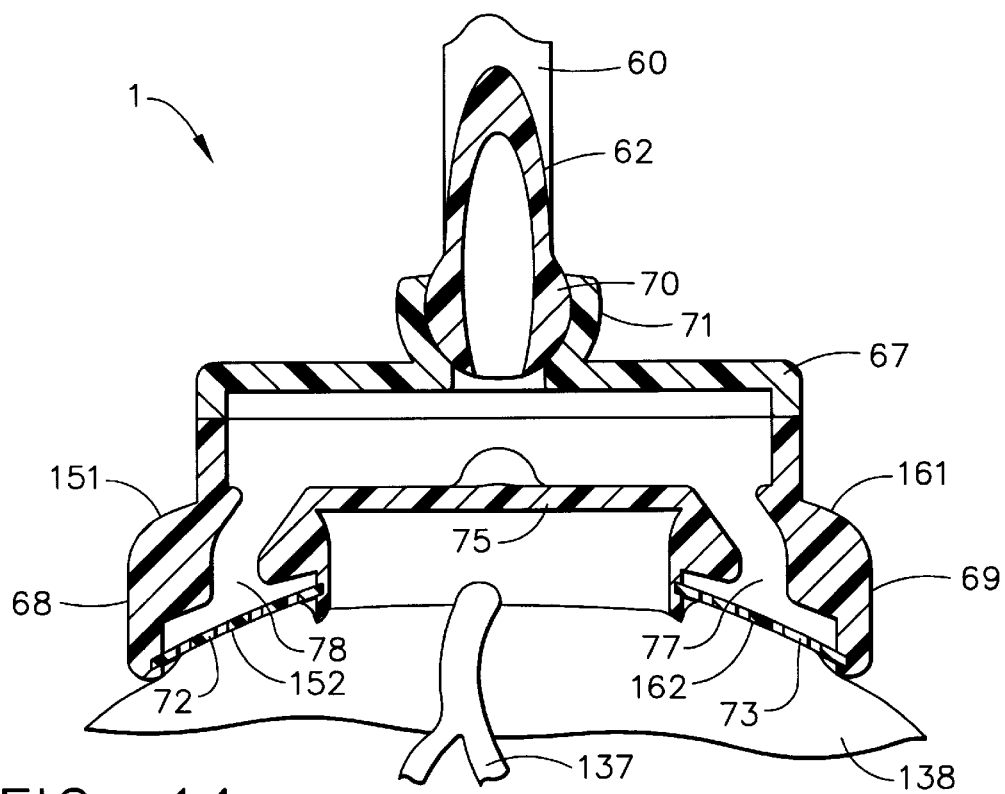
FIG. 11 shows a cross-sectional view of the distal portion of the stabilizer depicted in FIG. 10.

FIG. 11 is a cross-section of the distal portion of the stabilizer 1 shown in FIG. 10. As seen from the figure, device 1 includes at least one, and preferably a pair of feet 68 and 69, attached to the distal end 62 of tube 60. Each foot extends laterally outwardly from tube 60. Feet 68 and 69 have non planer-curved proximal surfaces 151 and 161, and a non-planer curved distal surface 152 and 162. Distal surfaces 152 and 162 make contact, direct or indirect, with the organ when in use with the vacuum. As shown in the figure surfaces 152 and 162 are in contact with an organ 138 having a vessel 137 located midway between the left and right feet 68, 69. The air passages through it can be seen as well as the left and right foot filters 73, 72 on distal surfaces 152 and 162 which reside in grooves in the left and right feet 69, 68 respectively. Filters 72 and 73 help prevent particulate material from entering tube 60 and causing a failure of the device. They also prevent the tissue surface from covering the left and right orifices 77 and 78.

Figure 12:
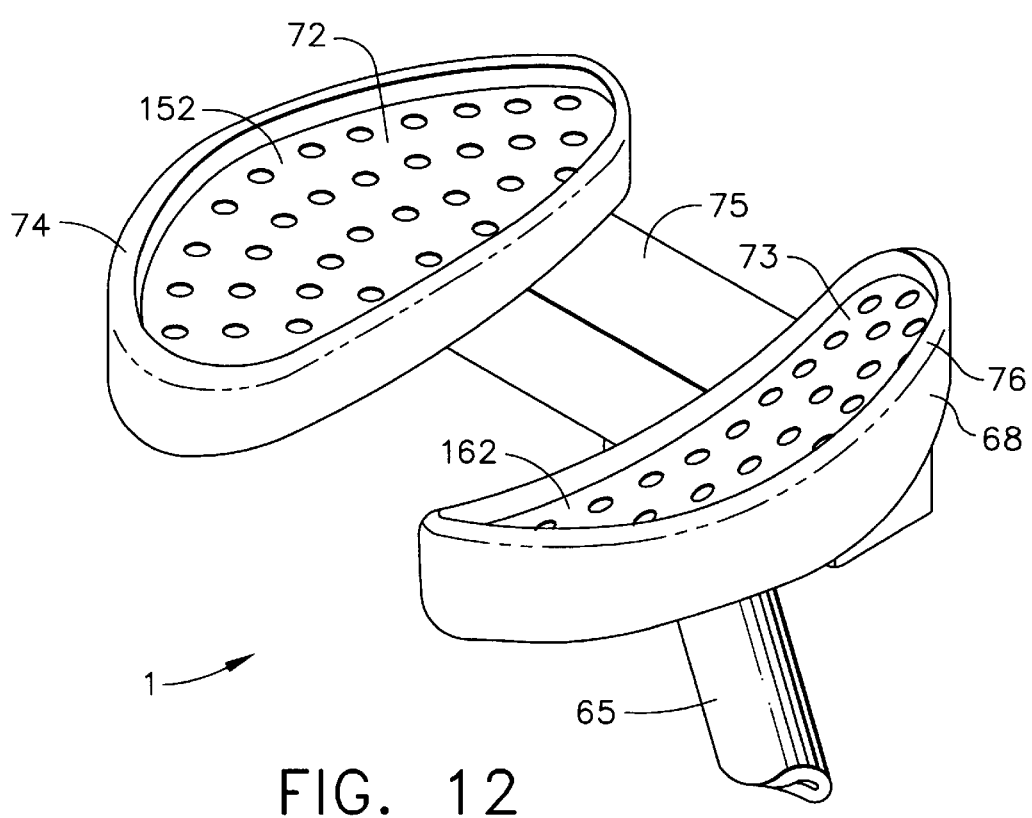
FIG. 12 is a perspective, bottom view of the distal portion of the stabilizer depicted in FIG. 1.

FIG. 12 is a bottom, perspective view of the distal portion of the stabilizer 1 of FIG. 1, giving another view of the right and left foot filters 72, 73 assembled into the feet 69, 68. The foot filters 72, 73 can be a mesh type of structure and may be a metal such as stainless steel or a plastic such as polycarbonate. They contain a plurality of holes sized largely enough and spaced in a manner to allow suction of the air from within the space between the organ surface and each screen, yet small enough to prevent tissue from blocking the suction passage through the left and right feet 68,69.

FIGS. 11, 12 also show how the left and right feet 69, 68 have outer perimeter edges 74, 76 which together can seal upon an essentially convex surface such as on the heart. For the enhanced attachment of the left and right feet 68, 69 to the organ surface by means of the evacuation of air and fluids from within, it is preferred that the feet perimeter edges 74, 76 remain in contact with the organ as it moves or is being manipulated. The embodiment shown in FIGS. 11, 12 has the feet perimeter edges 74, 76 defining a partial, spherical surface, that is they have a spherical profile, which has a radius of about the size of an orange, but this concavity may also vary in its depth and configuration. Another advantage of this embodiment is that the surface of the tissue in the span between the left and right feet 68, 69 is tensioned slightly, thus further stabilizing the vessel 137 or other tissue of interest to the surgeon.

Figure 16:
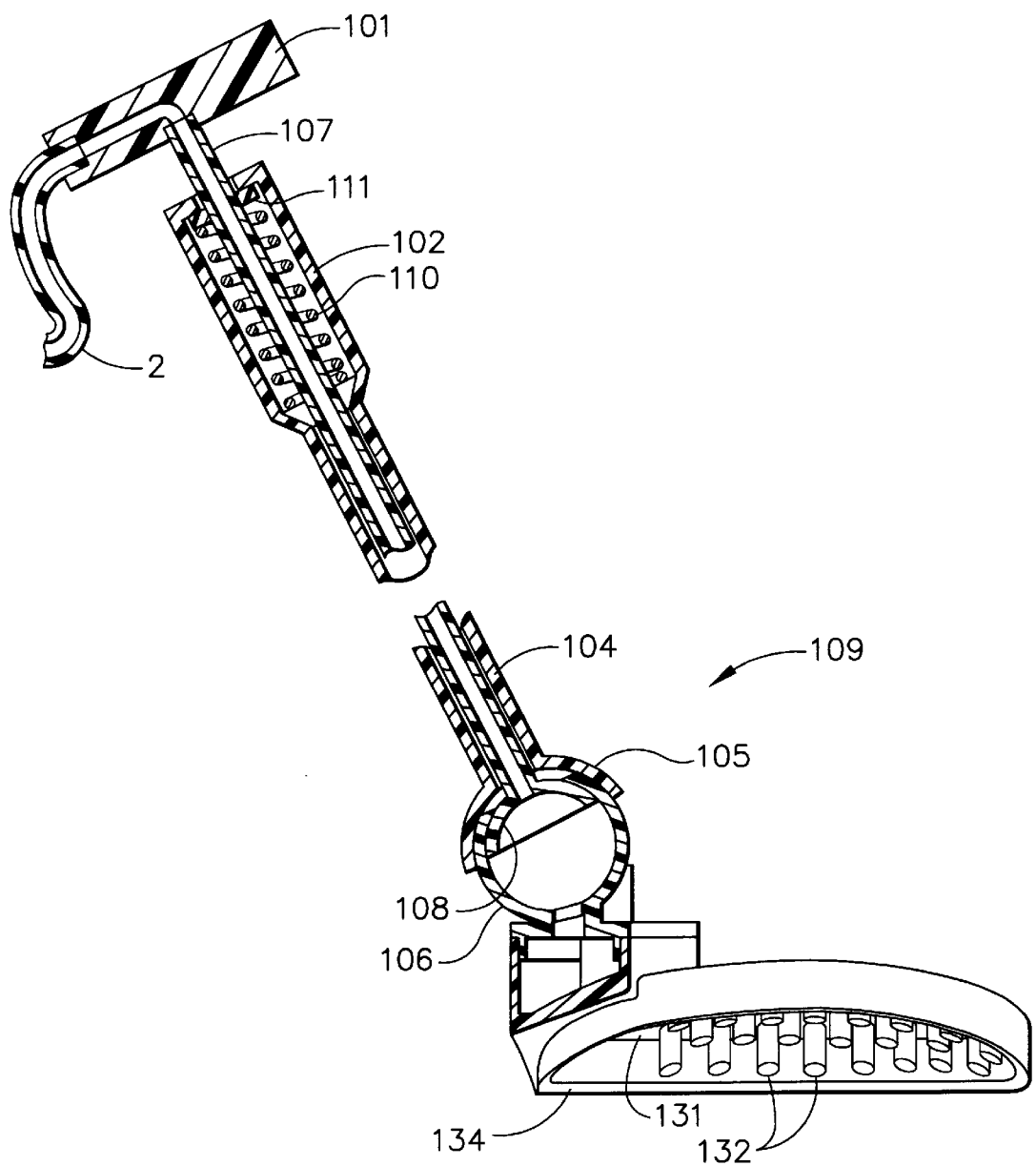
FIG. 16 is a partial cross-sectional view of the embodiment of the present invention shown in FIG. 15, showing an alternative embodiment of the distal portion of the stabilizer.

FIG. 16 shows a second embodiment of the distal portion of the present invention. Separate components for holding tissue away from the suction orifices 77, 78 (FIG. 11) have been replaced a plurality of pegs extending outwardly from the proximal surface of the feet 130 and 131. While only left foot 131 is shown, right foot 130 is a mirrored configuration of foot 131. The pegs 132 are preferably cylindrical and parallel to one another as shown in this embodiment, but may vary in size, spacing, and orientation. The tips extend to a length slightly proximal to the imaginary, concave surface described and provide atraumatic contact with the organ as it is pulled into the feet 130, 131 by the suction force. The surface of the organ 138 may tent into the interstitial spaces between the projections 132, thus adding the benefit of increased resistance to sliding of the stabilizer feet 130, 131 in the side-to-side directions. The projections 132 are spaced sufficiently distant from perimeter edges 74, 76 to allow the organ surface to seal properly against the left and right feet 69, 68. In addition, the pegs create a tortuous path for any particulate and therefore also act as a filter.

Figure 13:
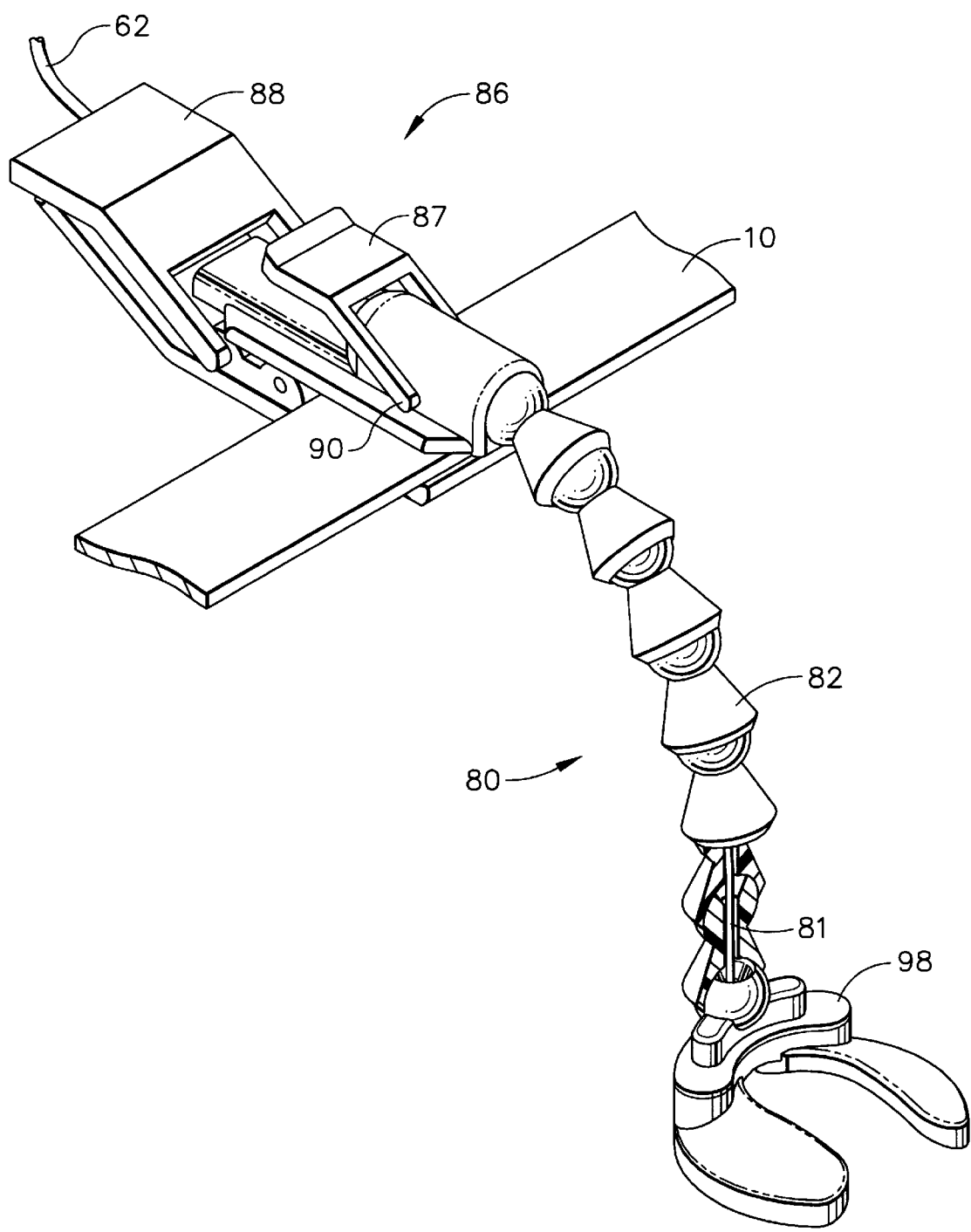
FIG. 13 shows an alternate embodiment of the present invention while it is attached to a retractor (partial view), showing a gooseneck style stabilizer connected to a draw latch retractor mount.
Figure 14:
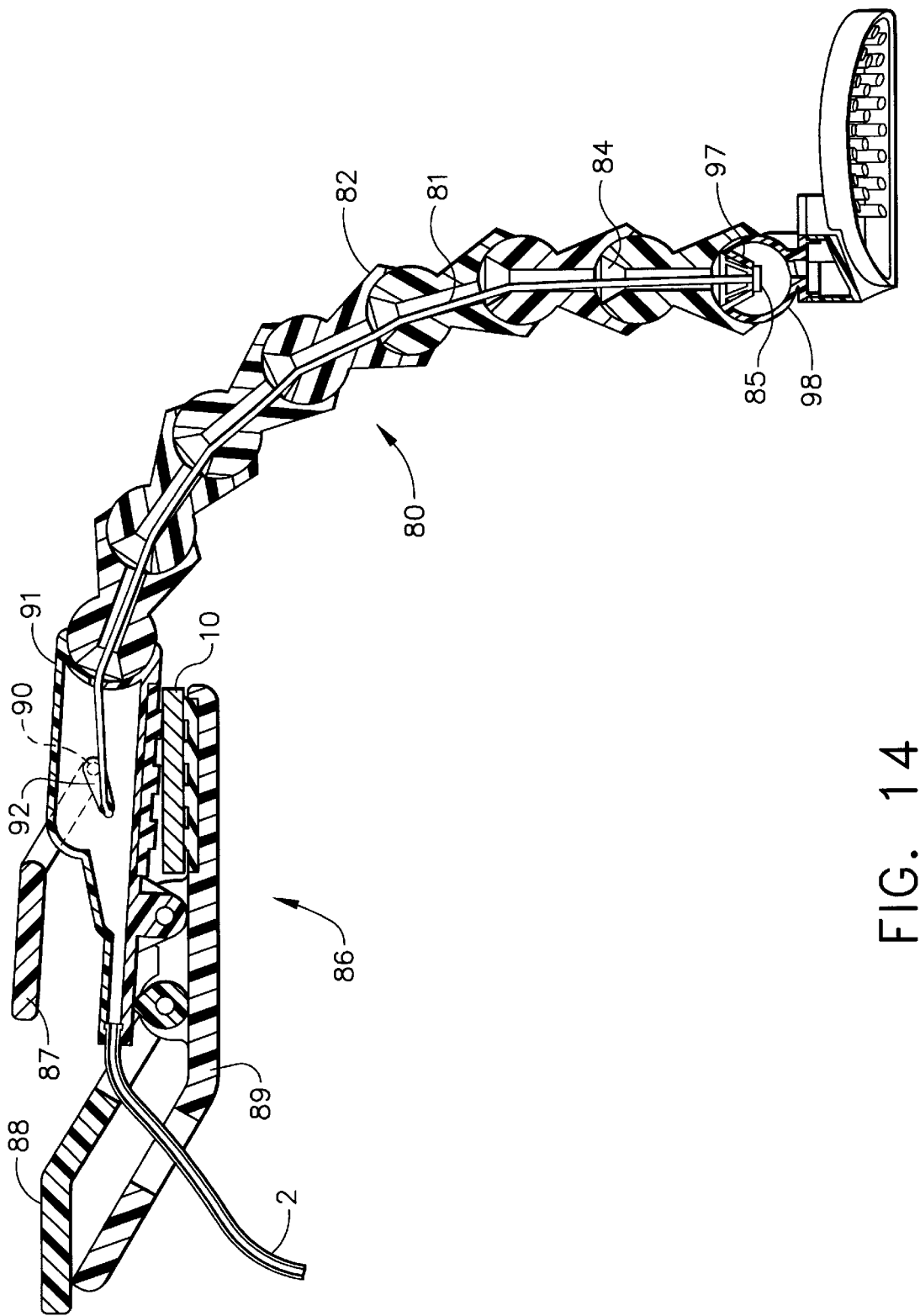
FIG. 14 shows a cross-sectional view of the alternate embodiment of the present invention depicted in FIG. 13.

FIG. 13 is a perspective view of another alternate embodiment of the present invention. The primary difference from the preferred embodiment shown in FIG. 1 is the increased, position flexibility, due to gooseneck 80 consisting of a plurality of ball/socket connectors 82. A retractor mount 86 clamps onto the retractor crossbar 10 as before using cam lever 88, but the mount differs in that it has a drawlatch 87 for tensioning/untensioning cable 81 for locking/unlocking the hold for the orientation of the gooseneck 80. FIG. 14 further depicts this embodiment, showing the air passages within and the interactions of the components as the retractor mount is clamped onto crossbar 10 and the gooseneck 80 is locked into orientation. The distal end of cable 81 is terminated with swaged fitting 85 which abuts against a spider-like internal retention feature 97 of the manifold 98. Tension in cable 81 is created when drawlatch 87 is squeezed against base 89, pivoting about drawlatch pivot 90, causing drawlatch hook 92 to swing over center of pivot 90. Reversal of this process releases the tension and allows the surgeon to reposition the gooseneck 80. In this embodiment, flexible hose 2 is attached to mount top 91. The number and size of ball/socket elements may vary and may be made of metal or plastic.

Figure 15:
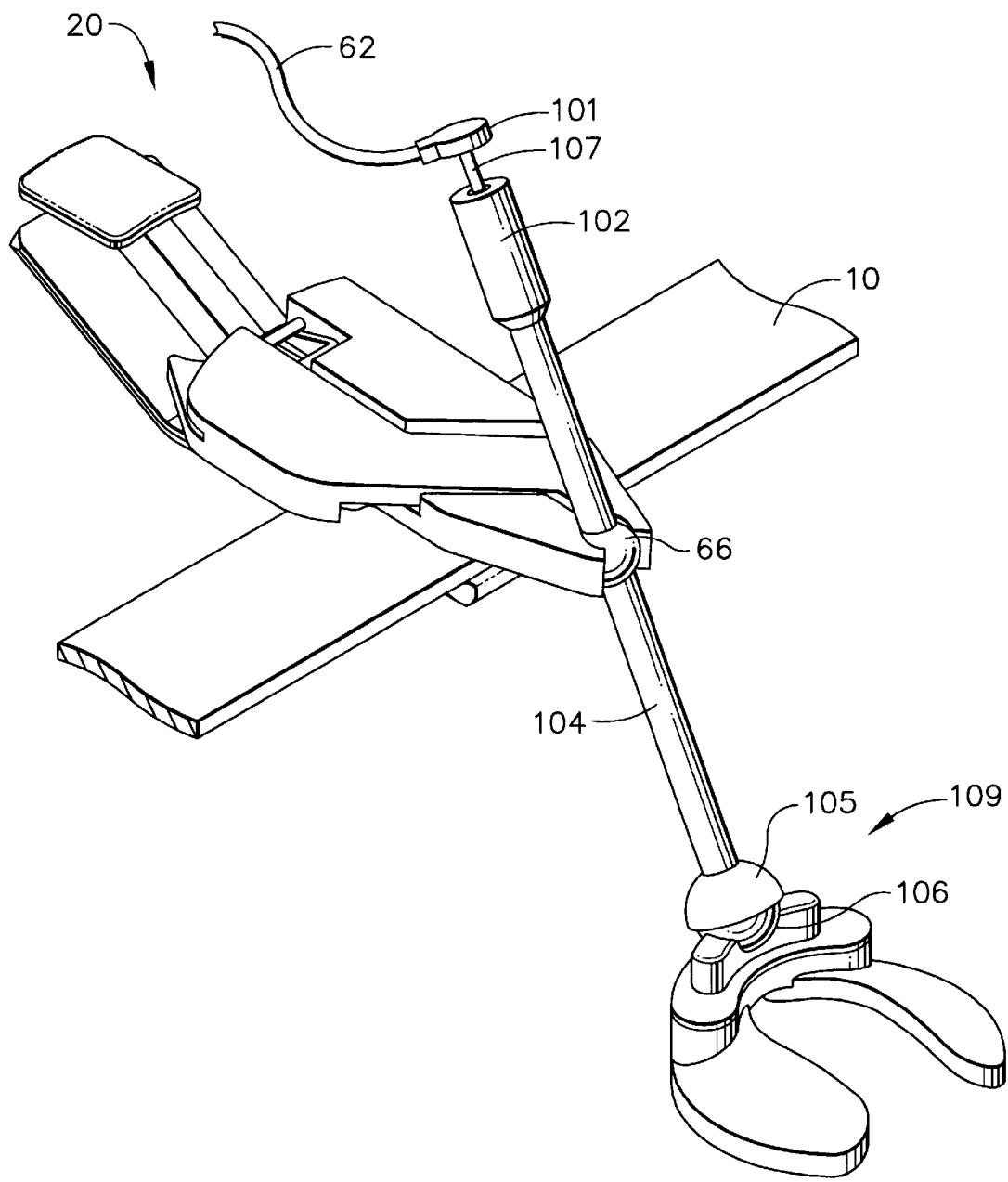
FIG. 15 shows a perspective view of another alternate embodiment of the present invention.

Referring to FIG. 15, another alternate embodiment of the present invention is shown in perspective view. A remote actuator 101 has been provided for locking the ball joint 109 on the distal end of the outer shaft 104. The surgeon can release the tightness of the ball joint 109 by squeezing together remote actuator 101 and the outer shaft proximal end 102. Upon release, the ball joint 109 is tight again and the stabilizer maintains its orientation. FIG. 16 is a cross-sectional view of the embodiment depicted in FIG. 15, and shows the air passage through it. The locking force is provided by coil spring 110 pushing on inner shaft flange 111. The stabilizer orientation is maintained by the frictional forces between components 105, 106, and 108 which are the shaft socket, manifold socket, and bell flange 108 on the distal end of inner shaft 107. A proximal ball 66 slides and rotates freely on shaft 104 in a similar manner as described in the preferred embodiment in FIG. 1. The retractor mount used for this embodiment would be the same as the one described in the preferred embodiment of FIG. 1. Flexible hose 2 attaches to remote actuator 101. Providing a remote actuator proximal to ball and socket joint 109, which is remote, or proximal to the joint 109 is advantageous in that the surgeons hands do not obstruct the view or contact the organ being operated on.

Figure 17:
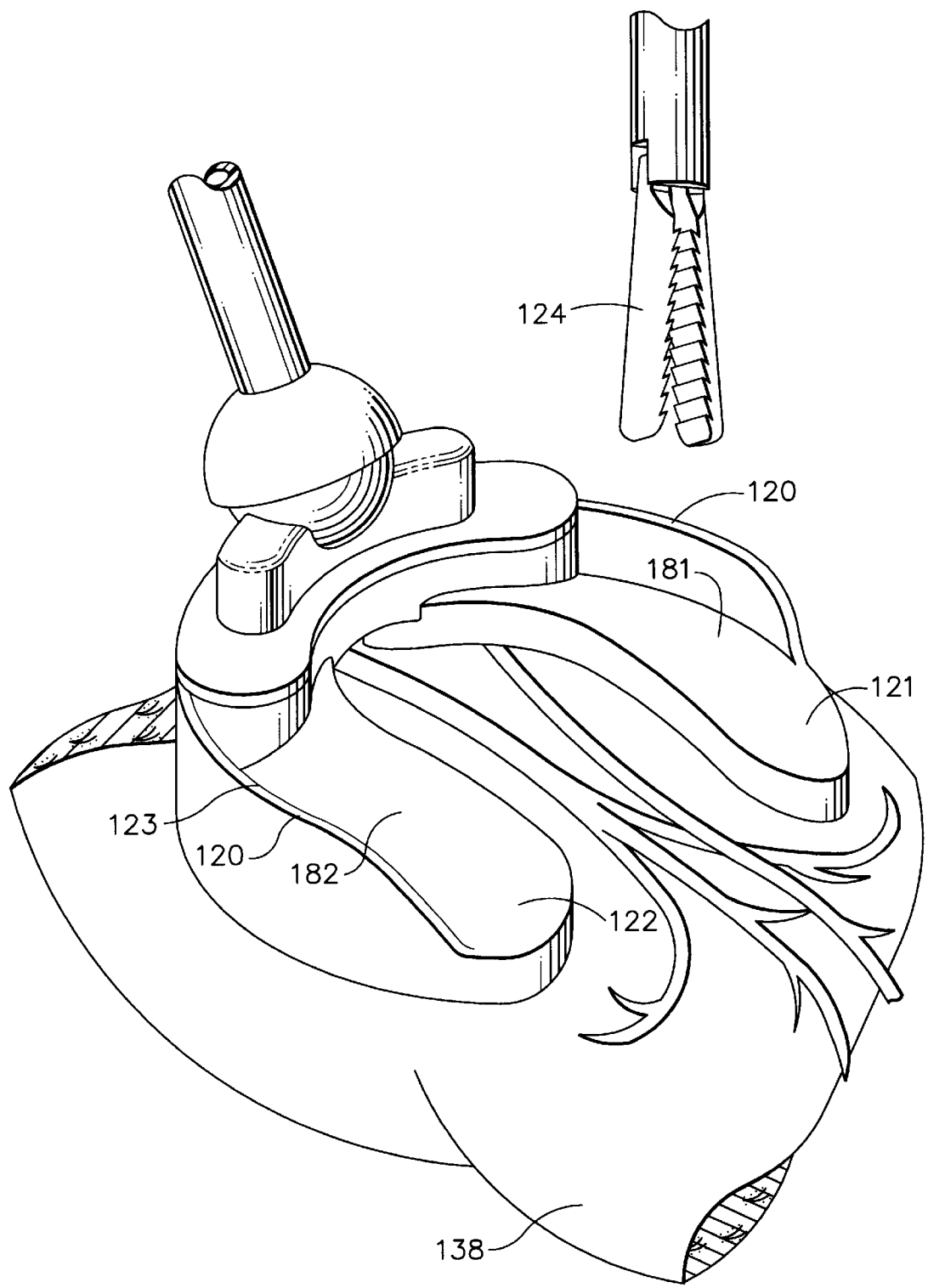
FIG. 17 shows another alternate embodiment of the distal portion of the stabilizer depicted in FIG. 2 as it is used in combination with a second, surgical, grasping device in surgery.

FIG. 17 is a perspective view of the distal portion of another alternate embodiment of the present invention, being used in combination with a second, surgical grasping instrument 124 for heart stabilization. In this embodiment, left and right flanges 120 and 123 have been added to the left and right feet 121, 122. Flanges 123 and 120 extend from proximal, or vertically, from the proximal surface 181 and 182 of the feet. The flanges provide a means of repositioning the distal portion of the stabilizer on the heart. Using the grasping instrument 124 allows the surgeon enhanced access and visibility to the surgical site, and aids in the precise positioning of the stabilizer feet. This is especially advantageous when operating through a narrow incision in the chest wall such as a mini-thoracotomy.

To further assist in the stabilization of the heart or other organ, other access retractors may also be used in conjunction with the present invention, such as spoon shaped probes to move other tissue from the surgical site.

Figure 18:
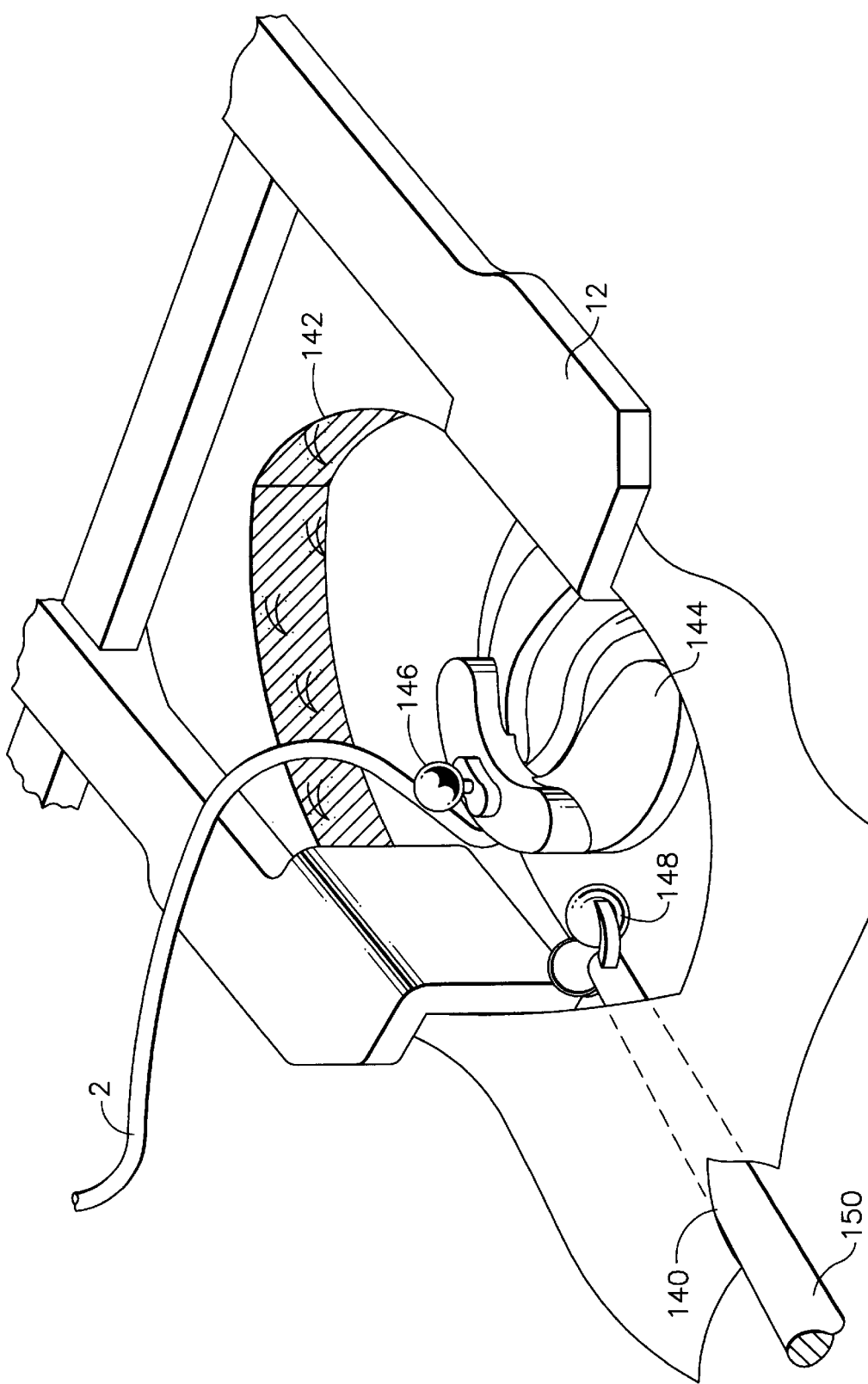
FIG. 18 is a bottom, perspective view of an alternate embodiment of the invention shown in FIG. 1.

Another alternate embodiment of the stabilizer, shown in FIG. 1 is depicted in FIG. 18. In this embodiment, the stem assembly 150 is detachable from the stabilizer foot assembly 144 so that the stem assembly may be introduced into the body and to the wound site through a separate, smaller incision 140 adjacent to the main incision 142. Once inserted, the stem assembly 150 is attached to stabilizer foot assembly 144 by means of a pair of cup-shaped graspers 148 clamping onto ball joint 146 or by various other means which allow angular variation of the stem assembly 150 with respect to the stabilizer foot assembly 144. The graspers 148 may be remotely actuated to open or close by a mechanism on the proximal portion of the stem assembly by various means also, such as is commonly used for endoscopic graspers and needle holders. It can be seen in FIG. 18 that the stabilizing foot assembly 144 is attached directly to a flexible, suction hose to enhance the attachment of the assembly to the organ. The stem assembly 150 may be hand held by the surgeon's assistant in order to stabilize the organ during the surgical procedure. It may also be used in combination with a trocar cannula with or without screwthreads to attach to the body wall, or with other kinds of trocars well known in the art. In addition, the proximal portion of stem assembly 150 may also be removably attached to the retractor 12 or other relatively stationary structures by means of various fixation devices which could easily be devised by those skilled in the art. The principal advantage of the embodiment of FIG. 18 is that the access to and visibility of the surgical site on the stabilized organ is improved because of the absence of the stem assembly 150 in the primary incision 142.

As disclosed, the present invention relates to a method and apparatus for stabilizing tissue. In the preferred embodiment, the invention is used to stabilize the heart tissue for a coronary artery bypass graft procedure using a surgical retractor, without the need for a cardiopulmonary bypass. The present invention and its alternate embodiments can be used for other surgical procedures, however, on organs such as stomach, lungs, etc. The present invention and its alternate embodiments have been described in detail, but it should be understood that variations and modifications can be incorporated within the scope of the following claims. These modifications may include substituting elements or components which have the same function to achieve the same result for those described herein.

What is claimed is:

1. A device for stabilizing moving tissue within the body, said device comprising:
   a) a tube having a proximal end, a distal end and a lumen extending therebetween, said tube is connected to a suction source so as to draw air through said tube from said distal end to said proximal end;
   b) at least one foot connected to said distal end of said tube, each foot extending laterally from said tube, each foot having a non-planer curved proximal surface, and a non-planer curved distal surface for placement adjacent to said tissue wherein said distal surface of each foot has an outer perimeter having a three dimensional concave substantially spherical profile which is curved in three dimensions.

2. The device according to claim 1 wherein said distal surface of each foot has a mesh member having a plurality of apertures extending therethrough, said apertures being smaller than an opening into said tube foot, whereby particulate material is substantially prevented from entering said lumen of said tube.

3. The device according to claim 1 further including a means for attaching the device to a stationary object.

4. The device according to claim 3 wherein said tube is attached to said means for attaching the device to a stationary object by a ball and socket connector.

5. The device according to claim 4 wherein said tube is readily and manually detachable from said means for attaching the device to a stationary object.

6. The device according to claim 1 wherein each foot is attached to said tube by a ball and socket connector.

7. The device according to claim 6, wherein said ball can be released from engagement with said socket by an actuator, said actuator being proximal to said ball and socket.

8. The device according to claim 1 wherein said tube is malleable.

9. The device according to claim 1 wherein said tube is a goose-neck comprising a plurality of segments connected to one another by ball and socket connectors.

10. A device for stabilizing moving tissue within the body, said device comprising:
    a) a longitudinal member having a proximal end and a distal end;
    b) at least one foot connected to said distal end of said member, each foot extending laterally from said member, each foot having a non-planer curved proximal surface, and a non-planer curved distal surface for placement adjacent to said tissue, wherein said distal surface of each foot has an outer perimeter having a three dimensional concave substantially spherical profile which is curved in three dimensions.

11. The device according to claim 10 further including a means for attaching the device to a stationary object.

12. The device according to claim 11 wherein said member is attached to said means for attaching the device to a stationary object by a ball and socket connector.

13. The device according to claim 12 wherein said member is readily and manually detachable from said means for attaching the device to a stationary object.

14. The device according to claim 13 wherein each foot has a proximal surface, and a distal surface for making contact with said tissue, said distal surface comprising a plurality of spaced apart pegs extending from said proximal surface.

15. The device according to claim 10 wherein each foot is attached to said member by a ball and socket connector.

16. The device according to claim 10 wherein said member is malleable.

17. The device according to claim 10 wherein said member is a goose-neck comprising a plurality of segments connected to one another by ball and socket connectors.

18. A device for stabilizing moving tissue within the body, said device comprising:
    a) a tube having a proximal end, a distal end and a lumen extending therebetween, said tube is connected to a suction source so as to draw air through said tube from said distal end to said proximal end;
    b) a pair of feet connected to said distal end of said tube, each foot extending laterally from said tube, each foot having a non-planer curved proximal surface, and a non-planer curved distal surface for placement adjacent to said tissue wherein said distal surface of each foot has an outer perimeter having a three dimensional concave substantially spherical profile which is curved in three dimensions.

19. The device according to claim 18 wherein said distal surface of each foot has a mesh member having a plurality of apertures extending therethrough, said apertures being smaller than an opening into said tube foot, whereby particulate material is substantially prevented from entering said lumen of said tube.

20. The device according to claim 18 further including a means for attaching the device to a stationary object.

21. The device according to claim 20 wherein said tube is attached to said means for attaching the device to a stationary object by a ball and socket connector.

22. The device according to claim 21 wherein said tube is readily and manually detachable from said means for attaching the device to a stationary object.

23. The device according to claim 18 wherein each foot is attached to said tube by a ball and socket connector.

24. The device according to claim 23, wherein said ball can be released from engagement with said socket by an actuator, said actuator being proximal to said ball and socket.

25. The device according to claim 18 wherein said tube is malleable.

26. The device according to claim 18 wherein said tube is a goose-neck comprising a plurality of segments connected to one another by ball and socket connectors.

27. A device for stabilizing moving tissue within the body, said device comprising:
    a) a longitudinal member having a proximal end and a distal end;
    b) a pair of feet connected to said distal end of said member, each foot extending laterally from said member, each foot having a non-planer curved proximal surface, and a non-planer curved distal surface for placement adjacent to said tissue, wherein said distal surface of each foot has an outer perimeter having a three dimensional concave substantially spherical profile which is curved in three dimensions.

28. The device according to claim 27 further including a means for attaching the device to a stationary object.

29. The device according to claim 28 wherein said member is attached to said means for attaching the device to a stationary object by a ball and socket connector.

30. The device according to claim 28 wherein said member is readily and manually detachable from said means for attaching the device to a stationary object.

31. The device according to claim 28 wherein each foot has a proximal surface, and a distal surface for making contact with said tissue, said distal surface comprising a plurality of spaced apart pegs extending from said proximal surface.

32. The device according to claim 27 wherein each foot is attached to said tube by a ball and socket connector.

33. The device according to claim 27 wherein said member is malleable.

34. The device according to claim 27 wherein said member is a goose-neck comprising a plurality of segments connected to one another by ball and socket connectors.

* * * * *